July 2, 1957 J. MARTINEZ Plant Pat. 1,616
ROSE PLANT
Filed Nov. 6, 1956
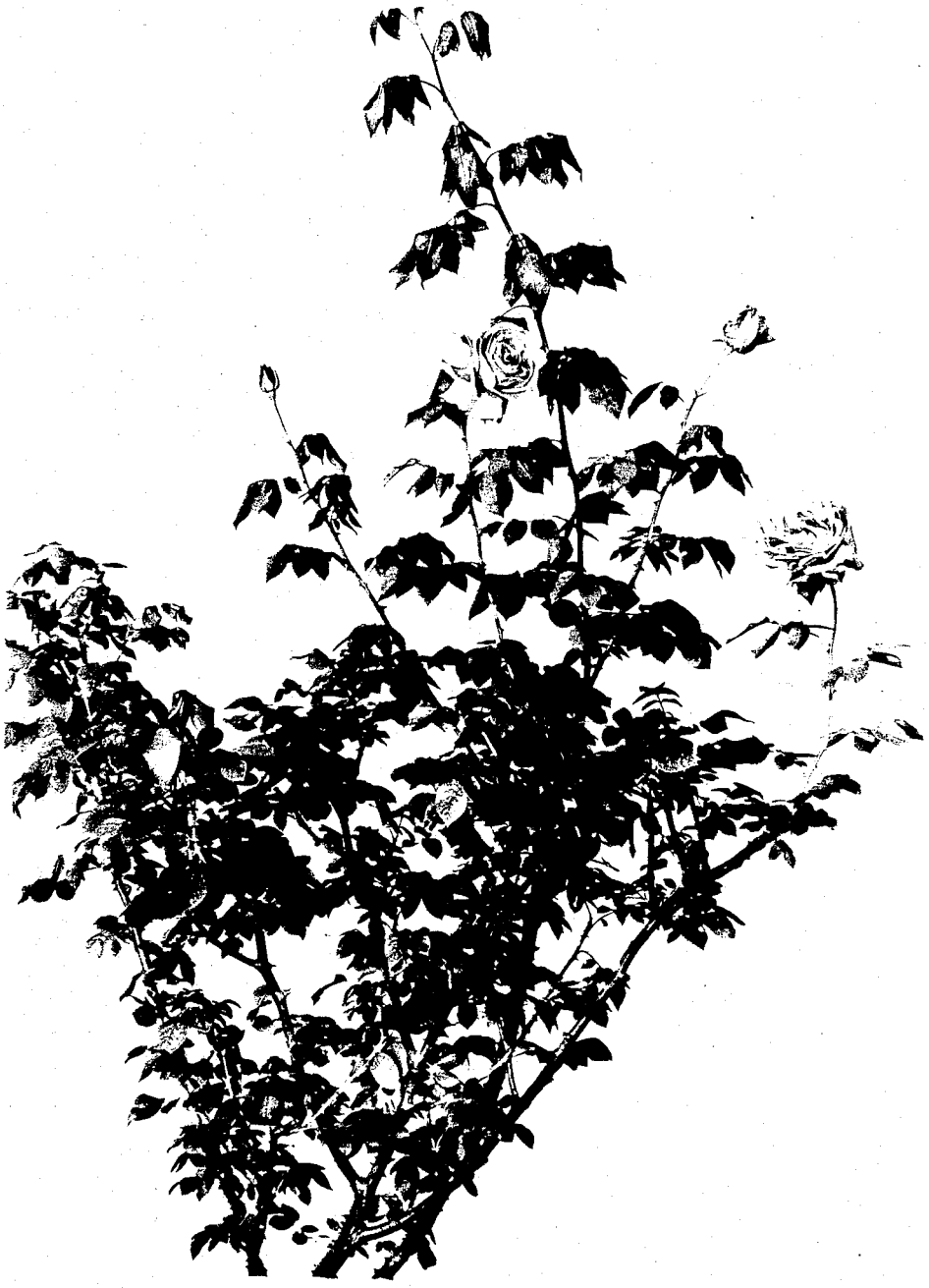
Inventor.
John Martinez
By: Robb & Robb
Attorneys.

United States Patent Office

Plant Pat. 1,616
Patented July 2, 1957

1,616

ROSE PLANT

John Martinez, Glendale, Ariz., assignor to Jackson & Perkins Company, Newark, N. Y., a corporation of New York Application November 6, 1956, Serial No. 620,777

1 Claim. (Cl. 47—61)

The present invention relates to a new and distinct variety of rose plant of the climbing floribunda class, which was discovered by me as a sport of the variety "Spartan" (Plant Patent No. 1,357).

The new variety was discovered by me in the fields of my assignee at Glendale, Arizona, where a block of plants of the variety "Spartan" were being grown. At the time of my discovery, my attention was attracted thereto by the fact that one plant in the block aforementioned exhibited a climbing habit of growth, as evidenced by sending out long basal shoots, while all other plants of the block of "Spartan" remained in the usual bush form. Upon closer observation, I found that the plant to which my attention had been attracted had sported, and I thereupon took steps to preserve the same, keep it under observation, and later asexually reproduce the sport. These observations and asexual reproductions as performed by me by budding at Glendale, Arizona, conclusively established that the climbing habit was fixed and capable of being transmitted through succeeding propagations.

I have found that the long basal shoots of the new sport attain a height of 6 or 7 feet during the first year, and these shoots produce lateral blooming spikes continuously throughout the growing season. The blooms and foliage generally correspond in form and color to those of the parent variety, "Spartan," which is a floribunda rose and has never previously exhibited a climbing habit so far as I am aware.

In addition to the climbing habit aforementioned, the new sport is further characterized by its mass of color which its flowers display, usually in the month of June, with the general color tonality corresponding to Rose Doree, lightly overcast with Scarlet, and the repeating clusters of bloom which occur on the ends of the long basal shoots and the side branches thereof throughout the growing season, all of which is unusual in a climbing rose of this color.

In view of the similarities in general characteristics between the new variety and its parent, except for the aforementioned distinctions, it is unnecessary to describe the new variety in detail, since it substantially conforms to the detailed description embodied in Plant Patent No. 1,357, dated March 1, 1955, to which reference may be readily had.

For convenience, the accompanying drawing shows in black-and-white a specimen plant of the new variety and is illustrative of the typical climbing habit of its growth.

I claim:

A new and distinct variety of rose plant of the climber class, substantially as herein shown and described, characterized particularly as to novelty by its general similarity to its parent variety "Spartan" (Plant Patent No. 1,357), but being essentially distinguished therefrom by its climbing habit of growth as evidenced by its long basal shoots which usually attain a height of about 6 or 7 feet during the first year and which send out lateral blooming spikes continuously throughout the growing season, with flowers being borne on both the terminal ends of the basal shoots and the lateral spikes, said flowers usually displaying a mass of color generally corresponding to the flowers of the parent variety aforementioned in the month of June, with repeating clusters of bloom throughout the remainder of the growing season.

No references cited.